United States Patent [19]

Anthony

[11] Patent Number: 5,172,686
[45] Date of Patent: Dec. 22, 1992

[54] DEVICE FOR SUPPLYING AIR OR MEDICAL GASES IN A CONDITIONED, PARTICULARLY A MOISTENTED AND/OR HEATED STATE TO A PATIENT

[76] Inventor: Jean-Michel Anthony, Ringlaan 78, 2610, Wilrijk, Belgium

[21] Appl. No.: 409,244

[22] Filed: Sep. 19, 1989

Related U.S. Application Data

[63] Continuation-in-part of Ser. No. 07/087,613, Aug. 20, 1987, abandoned.

[51] Int. Cl.⁵ ............................................. A61M 15/00
[52] U.S. Cl. ......................... 128/203.16; 128/203.27; 128/204.77
[58] Field of Search ...................... 128/200.11, 200.13, 128/203.16, 203.17, 203.26, 203.27, 204.13, 204.17

[56] References Cited

U.S. PATENT DOCUMENTS

| | | | |
|---|---|---|---|
| 1,043,689 | 11/1912 | Gottlieb | 128/204.13 |
| 3,881,482 | 5/1975 | Lindholm | 128/204.13 |
| 4,090,513 | 5/1978 | Togawa | 128/204.13 |
| 4,110,419 | 8/1978 | Miller | 128/203.27 |
| 4,303,601 | 12/1981 | Grimm et al. | 128/204.13 |
| 4,366,105 | 12/1982 | Nowacki | 128/204.13 |
| 4,381,267 | 4/1983 | Jackson | 128/204.13 |
| 4,674,494 | 6/1987 | Wieneck | 128/203.16 |
| 4,682,010 | 7/1987 | Drapeau et al. | 128/203.27 |

Primary Examiner—Lee S. Cohen
Assistant Examiner—John P. Lacyk
Attorney, Agent, or Firm—Scully, Scott, Murphy & Presser

[57] ABSTRACT

A device for supplying air or medical gases in a conditioned, particularly a moistened and/or heated state to a patient, through an air pipe. The device includes at least one component to be connected to said air pipe, the component being formed by a cylinder-shaped element with an inner tube through which the moistened air flows, which cylinder-shaped element is fitted with self-regulating heating resistors which heat the air flowing through the tube, while the cylinder-shaped tube from one element at least is filled with a material which adsorbs or absorbs the water supplied by a water-supply line from a container, and has a good air-permeability.

5 Claims, 1 Drawing Sheet

DEVICE FOR SUPPLYING AIR OR MEDICAL GASES IN A CONDITIONED, PARTICULARLY A MOISTENTED AND/OR HEATED STATE TO A PATIENT

CROSS-REFERENCE TO RELATED APPLICATIONS

This is a continuation-in-part of parent application U.S. Ser. No. 087,613 filed Aug. 20, 1987, now abandoned.

BACKGROUND OF THE INVENTION

1. Field of the Invention

This invention relates to a device for supplying air or medical gases in a conditioned, particularly a moistened and/or heated state, to a patient through an air pipe.

2. Discussion of the Prior Art

Such devices are known and are generally comprised of a water tank which insures a water supply to a generally cylinder-shaped chamber to which a supply line for an air/oxygen mixture and a discharge line for the heated and moistened mixture are connected. Depending on the local circumstances and requirements, the length of the discharge line, that is the line to the patient, may not always be determined beforehand.

Whatever may be the care wherewith the electric resistors insure heating the moistened air mixture, the temperature inside the discharge line will unavoidably get lower as the discharge line becomes longer. The temperature of the moistened air or gas mixture which leaves said chamber will never correspond to the temperature of a mixture which is fed to the patient. In spite of safety thermostats being present, the temperature will vary within limits which are not always allowable.

The discharge line or air pipe from the chamber to the patient may not always be designed as a sterile unit. For instance, French Patent 7,442,206 discloses a device which is only interchangeable when replacing the conveying tube and the resistance-heater wire, as well as the thermometer and the moisture sensor. Such a device may thus hardly be thought of as "disposable" and does not fulfill elementary sanitary criteria.

SUMMARY OF THE INVENTION

An object of the invention is to provide a sanitary device working under absolutely sterile conditions, whereby air or medical gases may be fed in moistened conditions, or a heated state to a patient, and the heating and heat-regulating components of which do not have to be renewed every time that the air- or gas-conditioning components have to be replaced for sanitary reasons.

Another very important object of the invention is to provide a device which insures an accurate temperature regulating of the moistened air mixture being delivered.

To obtain this according to the invention, the device according to the invention comprises at least one component to be connected to said air pipe, which component is formed by a cylinder-shaped element with an inner tube through which the moistened air flows, which cylinder-shaped element is fitted with self-regulating heating resistors which heat the air flowing through said tube, while the cylinder-shaped tube from one element at least is filled with a material which adsorbs or absorbs the water supplied by a water-supply line from a container, and has a good air-permeability.

In a first possible embodiment, this material comprises fibers, while in another possible embodiment, the material comprises beads.

BRIEF DESCRIPTION OF THE DRAWINGS

Other details and advantages of the invention will stand out from the following description, given by way of non limitative example and with reference to the accompanying drawings, in which.

DETAILED DESCRIPTION OF THE PREFERRED EMBODIMENTS

Figure 1:
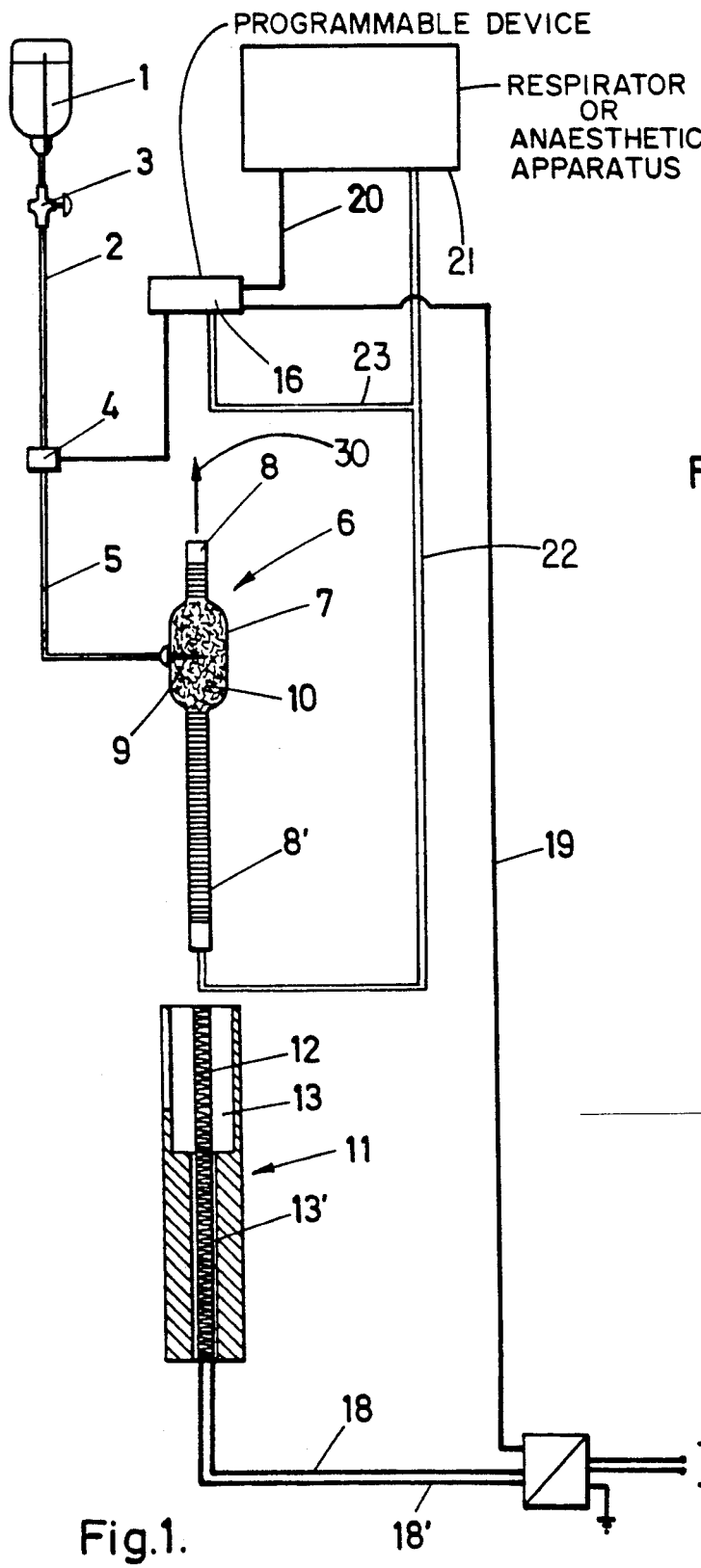
FIG. 1 illustrates a diagrammatic view of the preferred embodiment of the device according to the invention.

The device according to the invention comprises a container 1 for sterile water. Such a container may for example be a so-called "Baxter" type container. An electro-magnetic throttling valve 4 is mounted on the line 2 which extends from said container 1, beyond the usual regulating cock 3. Past said throttling valve, the line 5 runs to a tube 6 with an enlarged portion which forms a chamber 7 which is provided between two pipes 8 and 8'. When as it is preferred, tube 6 may be made from a synthetic material, so that the end of line 5 may be provided with a hollow needle 9 which can be pushed through the wall of tube 6, into chamber 7.

The tube 6 should be considered as being connected in the supply to the respirator or anaesthetic apparatus 21 of a patient. The purpose of the present invention is to furnish air in a moistened and heated state to a patient in connection with the respirator or anaesthetic apparatus 21 to which the patient is connected. The respirator or anaesthetic apparatus 21 feeds air to the patient through air duct 22 at tube 8'. Arrow 30 indicates the direction in which the moistened and/or heated air flows. Line 20 connects respirator apparatus 21 with programmable means 16, while branch 23 connects programmable means 16 with air duct 22 for pneumatically controlling respirator apparatus 21 to regulate the inspiration of air by the patient.

To let the required air volume through tube 6 and simultaneously insure optimum moistening thereof, the chamber 7 in tube 6 is filled with a material which may be provided in the shape of fibers or beads, as indicated by numeral 10. It is essential for the invention that said material adsorbs water on the surface or simply absorbs water, while still letting air through unhindered.

The tube 6, which forms a disposable unit, is intended to be slipped into the cylinder-shaped metal element 11. Cylinder-shaped element 11 comprises a self-regulating resistor 12 which runs along the inner wall from the wider passageway 13 and the passageway 13' for connection to the cylinder-shaped component. Resistor 12 thus lies in close contact with the wall of tube 6 and thus both with chamber 7 and pipes 8 and 8' thereof.

Figure 3:
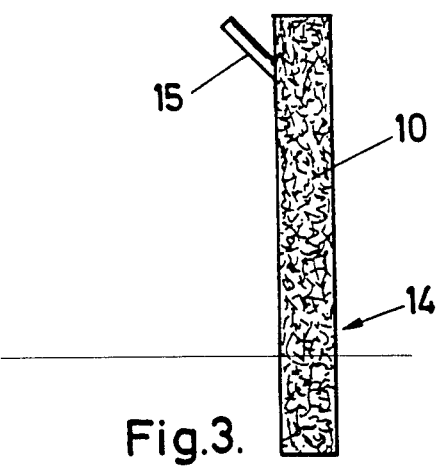
FIG. 3 illustrates a second variation in the same detail from the device according to the invention.

The disposable tube 6 may also be in the form of a cylinder 14 as shown in FIG. 3. The material is shown here also with reference numeral 10. The resistor for heating the water and the air flowing through, may be provided about said cylinder-shaped element, but it might also be arranged sidewise relative to said element.

The inlet for sterile water may take the form of a small tube 15. It is however clear that here also use may be made of a hollow needle 9, as shown in FIG. 1.

Figure 2:
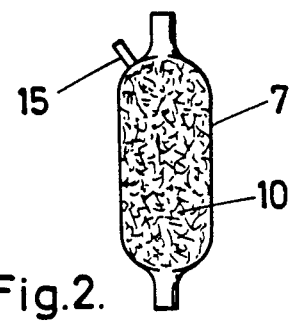
FIG. 2 illustrates a first variation in a detail from the device according to the invention.

The variation as shown in FIG. 2 differs but little from the embodiment as shown in FIG. 1, except for the provision of an inlet 15 as also provided in the variation as shown in FIG. 3.

Using the same principle, a plurality of elements fitted with self-regulating resistors may be connected together, or may be provided at the end of the "air pipe" which leads to a patient.

This provides for a constant temperature of the circulating moistened air and also to prevent condensation. The self-regulating heating resistors naturally insure the circulating air being maintained at a constant temperature. Each cylinder-shaped element which is being used comprises a continuous passage for a straight-through tube 6 and means whereby two such elements can be coupled to one another and the heating resistors thereof be connected together. Element 11 may also hingedly open and close along its length.

Since it is preferred that the materials of which the cylinder-shaped element and the tube are made are flexible at room temperature, it is possible to fold or bend the cylinder-shaped element with the tube provided therein. This thus allows for maintaining the temperature of the air flowing in the "air pipe" at the desired level, while adapting the "air pipe" profile to given requirements.

The invention further relates to the provision of programmable means 16 which controls the throttling valve and is connected to the respirator or anaesthetic apparatus shown in FIG. 1. The programmable means 16 makes it possible to synchronize the admission of water with the respiration of the patient. The respiration cycle of the patient can be detected by the programmable means 16 which controls throttling valve 4 so that the latter may supply for each registered respiration cycle a well defined amount of water to be delivered through line 5 to tube 6. This is important because the amount of water to be delivered to tube 6 can be determined exactly as a function of the variable respiration cycle of the patient. The programmable means 16 may function as a timer to actuate the respirator apparatus 21 at precise time intervals, to feed air from the throttle valve through air duct 22 to chamber 7. The programmable means 16 may also function pneumatically or receive an electrical signal from the respirator 21. In essence, the programmable means 16 may be a microprocessor-controlled or manually-actuatable timing device; for instance, with two timers, of which one determines the functioning frequency, and the other the opening period of time for the throttling valve 4. Such timing devices are readily commercially available and, consequently, not described in detail herein. Programmable means 16 guarantees that the amount of water delivered to the patient is always dependent on the amount of air inspirated by or delivered to the patient.

In the diagrammatic view according to figure 1, there is further illustrated a current source 17, lines 18 and 18' which lead to resistor 12, and reference numeral 19 which shows the line to programming means 16, while numeral 20 illustrates the line to and from the device remote control.

It appears very clearly from the above description of the device according to the invention, that the device of the present invention offers the following remarkable advantages:

1) a far-driven hygiene because the required water is collected into disposable sterile containers and is supplied through similar lines;

2) the same is valid for the containers wherein that material is enclosed which adsorbs the water in the shape of microscopic droplets on the surface;

3) due to the module-like design of the cylinder-shaped elements 6, a completely constant heated air-pipe circuit can be built-up; and 4) due to the provision of a programmable means and a throttling valve controlled by the programmable means, the possibility is given of obtaining a programmed operation of the device by the respirator or anaesthetic apparatus connected thereto. Such operation may also be synchronized with the respirator or anaesthetic apparatus of the patient.

It is clear that the invention is in no way limited to the above-described embodiment and that many changes might be brought thereto without departing from the scope of the invention.

What is claimed is:

1. Device for supplying air or medical gases in a conditioned state to a patient through an air pipe connected to a source for said air or gas, said device comprising at least one tube including said air pipe for the flow of said conditioned air therethrough, said tube having a flow chamber of a diameter which is larger than the diameter of the air pipe connected therewith, a container for a supply of water, said flow chamber in said tube being at least partly filled with a material which adsorbs or absorbs water conveyed into said flow chamber through a water-supply line leading from said container, an electromagnetic throttling valve interposed in said water-supply line, at least one cylinder-shaped element having a central passageway dimensioned to have said flow chamber and portions of said air pipe adjacent to junctures with said flow chamber inserted therein, heating resistors on said cylinder-shaped element regulating the temperature for the air or gas flowing through said tube, and programmable means operatively connected with said throttling valve, said source for supplying said air or gas and said heating resistors for controlling the operation of said throttling valve to synchronize the state in the condition of the air or gas conducted to the patient with the admission of water from said water-supply line to said tube.

2. Device as defined in claim 1, in which said material is present in the shape of beads.

3. Device as defined in claim 1, in which said material is present in the shape of fibers.

4. Device as defined in claim 1, in which said tube is made from a material adapted to be punctured by a hollow needle connected to said line for supplying water from said container.

5. Device as defined in claim 1, in which said at least one cylinder-shaped element and the tube are each constituted from a material which is flexible at room temperature.

* * * * *

UNITED STATES PATENT AND TRADEMARK OFFICE
CERTIFICATE OF CORRECTION

PATENT NO. : 5,172,686
DATED : December 22, 1992
INVENTOR(S) : Jean-Michel Anthony It is certified that error appears in the above-identified patent and that said Letters Patent is hereby corrected as shown below:

On title page, item [76], "Wilrijk" should read as --Wiltijk--

Column 3, lines 46-47, "respirator apparatus 21" should read as --throttle valve 4--

Column 3, lines 47-48: delete "air from the throttle valve through air duct 22" and insert --water--

Signed and Sealed this

Sixteenth Day of November, 1993

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,172,686
DATED : December 22, 1992
INVENTOR(S) : Jean-Michel Anthony It is certified that error appears in the above-indentified patent and that said Letters Patent is hereby corrected as shown below:

On the Title Page, item [76], "Wiltijk" should read --Wilrijk--

Signed and Sealed this

Eighteenth Day of July, 1995

Attest:

BRUCE LEHMAN

Attesting Officer

Commissioner of Patents and Trademarks